(12) United States Patent
Matsuoka et al.

(10) Patent No.: US 6,271,267 B1
(45) Date of Patent: Aug. 7, 2001

(54) COMPOUND TO REGULATE THE MORPHOLOGICAL TRANSITION OF DIMORPHIC CANDIDA

(75) Inventors: Hideaki Matsuoka, Musashino; Ki-Bong Oh, Koganei, both of (JP)

(73) Assignee: Bio-Giken, Inc., Chiba (JP)

( * ) Notice: Subject to any disclaimer, the term of this patent is extended or adjusted under 35 U.S.C. 154(b) by 0 days.

(21) Appl. No.: 09/316,087

(22) Filed: May 21, 1999

(30) Foreign Application Priority Data

Mar. 31, 1999 (JP) .................................................. 11-093427

(51) Int. Cl.[7] .................... A61K 31/045; A61K 31/01; A61K 31/22; A61K 31/20
(52) U.S. Cl. .......................... 514/739; 514/560; 514/546; 514/762
(58) Field of Search ...................................... 514/762, 739, 514/560, 546

(56) References Cited

U.S. PATENT DOCUMENTS

| | | | |
|---|---|---|---|
| 3,595,975 | 7/1971 | Gauvreau | 514/179 |
| 4,220,665 | 9/1980 | Klein | 514/739 |

OTHER PUBLICATIONS

Arai, T. et al., "Phagocytosis of *Candida albicans* by Rabbit Alveolar Macrophages and Guinea Pig Neutrophils," *Sabouraudia* 15, pp. 171–177 (1977).
Jorge Neto, Rev. Fac. Farm. Odontol. Araraquara, 10(2), 317–327, 1976.*
Duve et al., J. Insect. Physiol. , 38(8), 575–585, 1992.*
Andersen et al., Chem. Res. Toxicol., 10(2), 156–164, 1997.*
Lunz et al., Physiol. Entomol., 22(4), 365–372, 1997.*

* cited by examiner

*Primary Examiner*—David M. Naff
*Assistant Examiner*—Mike Meller

(74) *Attorney, Agent, or Firm*—Oliff & Berridge, PLC

(57) ABSTRACT

A method for regulating the morphological transition of dimorphic Candida in a patient is described. The method comprises administering orally or by injection a compound to a patient suffering from an infection caused by dimorphic Candida selected from the group consisting of *Candida albicans, Candida stellatoidea, Candida tropicalis, Candida grabrata*, and *Candida parapsilosis*. The compounds are used to regulate the morphological transition of the dimorphic Candida, wherein the compound is selected from the group consisting of:

(Compound 8)

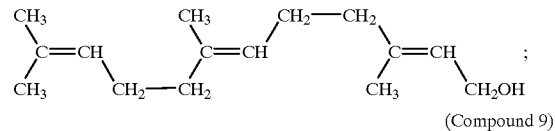

(Compound 9)

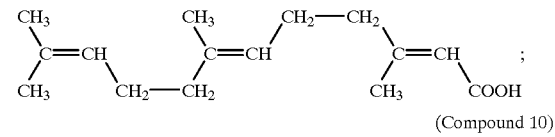

(Compound 10)

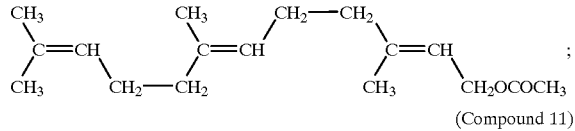

(Compound 11)

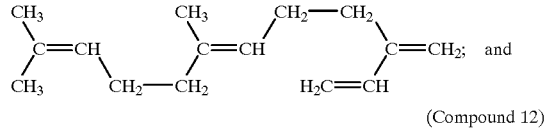

(Compound 12)

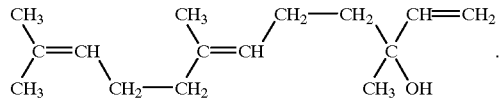

1 Claim, 10 Drawing Sheets

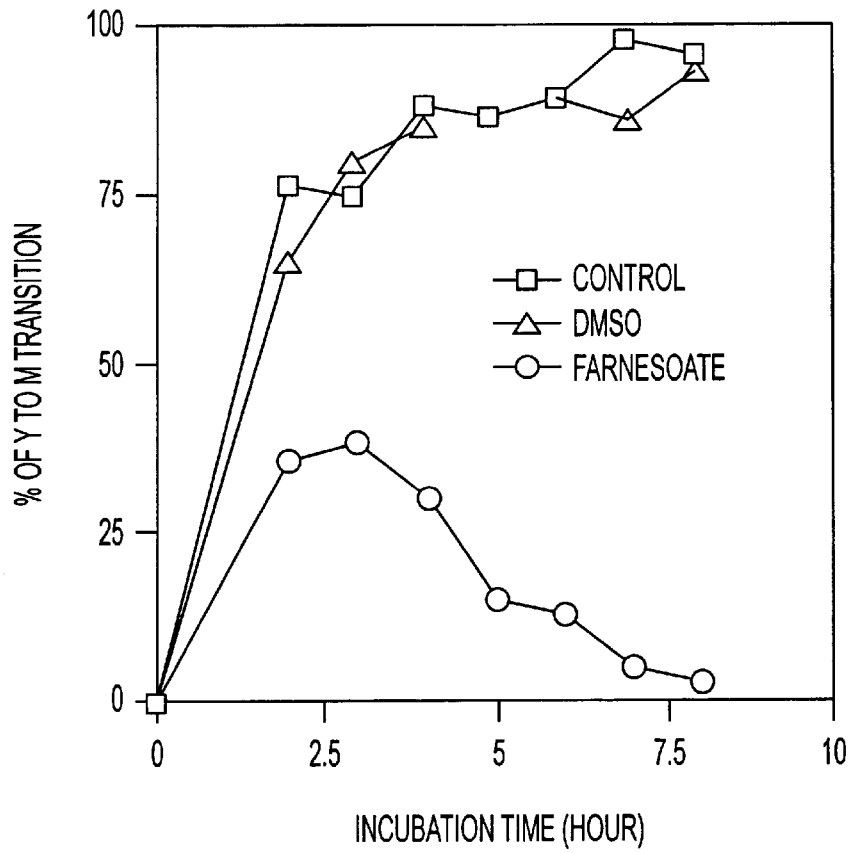
FIG. 1A
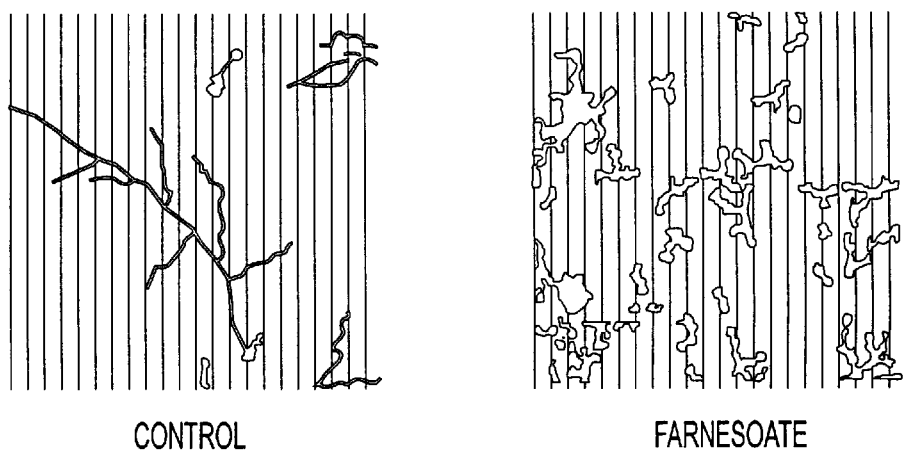
FIG. 1B  FIG. 1C

| REAGENT | $IC_{50}$ ON Y FORM CELLS AFTER 8 HOURS INCUBATION ($\mu$g/ml) | $IC_{50}$ ON Y TO M TRANSITION ($\mu$g/ml) | |
|---|---|---|---|
| | | AFTER 2 HRS INCUBATION | AFTER 5 HRS INCUBATION |
| FARNESOATE (COMPOUND 9) | $\geq 200$ | 100 | 3.12 |
| FARNESOL (COMPOUND 8) | $\geq 200$ | 3.12 | 0.4 |
| FARNESYL ACETATE (COMPOUND 10) | $\geq 200$ | 200 | 50~100 |
| β-FARNESENE (COMPOUND 11) | $\geq 200$ | 25 | $\geq 25$ |
| GERANIOL (COMPOUND 1) | $\geq 200$ | 200 | 100~150 |
| GERANYL GERANIOL (COMPOUND 13) | $\geq 200$ | 150~200 | 50~100 |

FIG. 10

COMPOUND TO REGULATE THE MORPHOLOGICAL TRANSITION OF DIMORPHIC CANDIDA

BACKGROUND OF THE INVENTION

1. Field of Invention

The present invention relates to agents having regulatory activity for the morphological transition of dimorphic fungi which can grow both as yeast form cells and as mycelial form cells.

2. Description of Related Art

Most fungi take the form, through their life cycle, of either a spherical single cell growing through budding (or cell division) (yeast form fungus) or a filamentous multicellular organism growing through apical growth (filamentous fungus). However, some yeasts can reversibly take yeast form (Y form) and mycelial form (M form). This phenomena in which such a reversible transition occurs due to a specific nutritional, physical or chemical factor is called as dimorphism. The dimorphic fungi generally belong to Subdivision Deuteromycotina. and typically include genus Candida. The dimorphic fungi such as genus Candida are indigenous microbes with respect to humans, which generally exist in human bodies or in a living environment. They are not pathogenic to healthy humans but become pathogenic to patients whose immunity is deteriorated by some cause, and such an infection is called as an opportunistic infection. By taking Candida albicans belonging to genus Candida as an example, it has been known, in fact, that a multiplicity of mycelial form cells are present in combination with yeast form cells in infectious foci of candidiasis, indicating that being mycelial form cells is one of the pathogenic factors of this fungi. This is supposedly because mycelia of the mycelium form cells readily adhere to animal tissues and advantageously serve to invade mechanically into the inside of host tissues, and in addition hardly suffer from mycophagy activities of phagocytes (Arai, T., et al., Sabouraudia 15, 171–177(1977)).

SUMMARY OF THE INVENTION

Practical findings on factors of the reversible transition between yeast form cells and mycelial form cells, however, have not yet been obtained. If mycelial form cells, which are considered to be pathogenic, can be transited to yeast form cells with efficiency, opportunistic infections caused by these dimorphic fungi may be mitigated. To patients whose biophylaxis functions are deteriorated, such as the elderly, patients with cancers, or patients who have been subjected to organ transplantation or those infected with HIV, a variety of antibiotics are administered for phylaxis against bacteria, but infections of molds, yeasts or other fungi induced by microbial substitution cannot be prevented under present circumstances. In particular, medically significant demands have been made to develop drugs that are effective to dimorphic fungi generally exiting in vivo and have less adverse drug reactions.

Accordingly, the present invention provides an agent having regulatory activity on the morphological transition of dimorphic fungi, which includes a compound containing at least one geranyl group represented by the following formula (1) as its main structure:

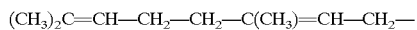

In this agent, the compound containing at least one geranyl group may preferably be a terpene or its isomer, or a derivative thereof.

The terpene in the above agent may be a monoterpene composed of one geranyl group, a sesquiterpene containing one geranyl group or a diterpene containing two geranyl groups.

In this agent, when the dimorphic fungi are genus Candida, the regulatory activity on morphologic transition may be inhibitory activity on transition of yeast form cells to mycelial form cells or promoting activity on transition of mycelial form cells to yeast form cells.

BRIEF DESCRIPTION OF THE DRAWINGS

These and other features, objects, and advantages of the present invention will become apparent upon a consideration of the following description of the invention when read in conjunction with the following drawings.

FIG. 1A is a diagram graphically illustrating percentages of the transition from Y form cells to M form cells when famesoate is added.

FIGS. 1B and 1C each represent photomicrographs illustrating cultures after 8 hours of incubation. FIG. 1B illustrates a Control culture and FIG. 1C illustrates a culture to which famesoate has been added.

FIG. 10 is a diagram demonstrating 50% inhibitory concentrations of compounds according to the invention on the growth of yeast form cells after 8 hours of incubation, and their 50% inhibitory concentrations on Y to M transition after 2 hours and 5 hours of incubation.

DETAILED DESCRIPTION OF PREFERRED EMBODIMENTS

Figure 2:
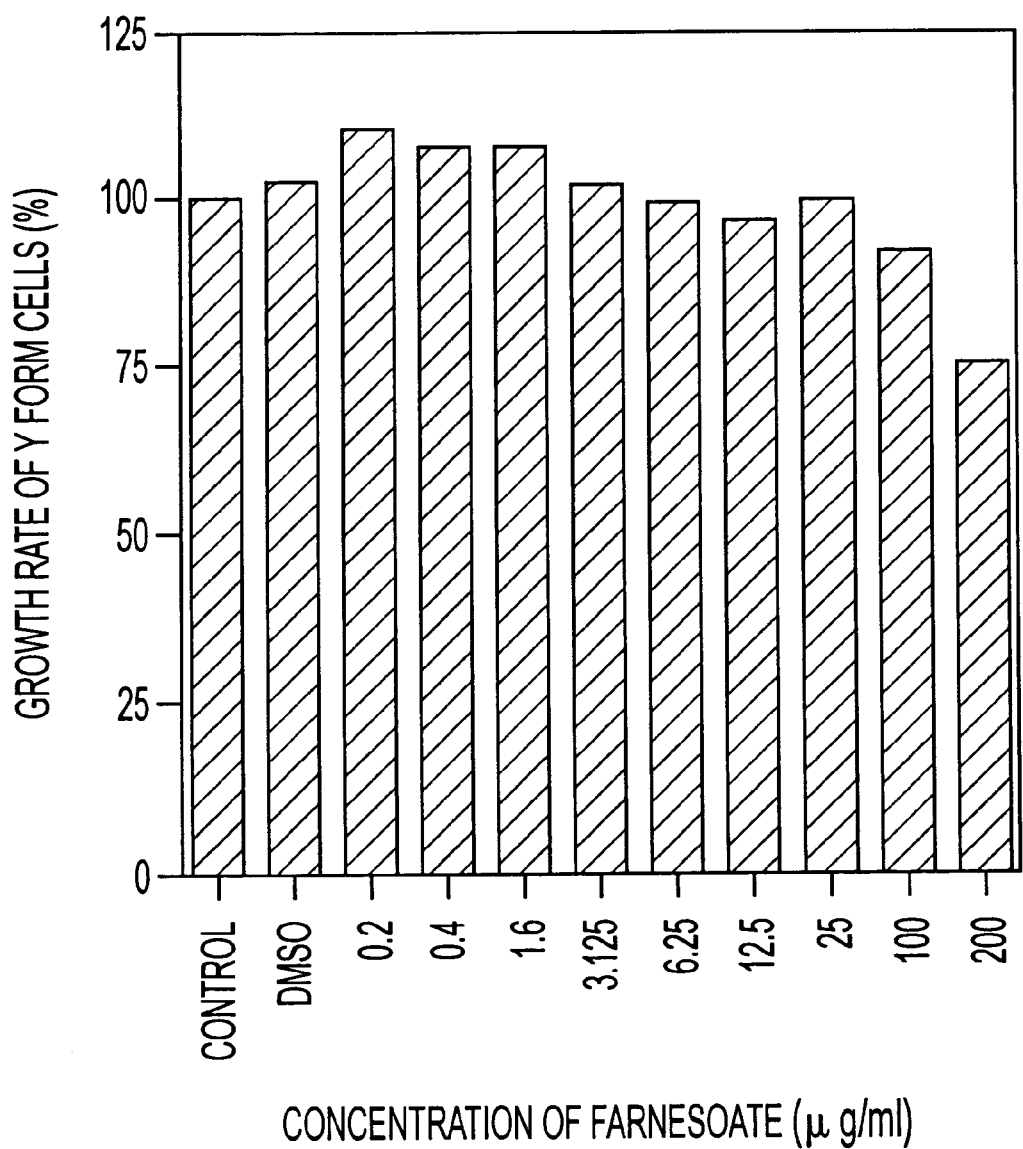
FIG. 2 is a diagram graphically illustrating inhibitory effect of farnesoate on the growth of yeast form cells after 8 hours of incubation.

The agent according to the invention comprises a compound containing at least one geranyl group represented by the following formula (1) as its main structure:

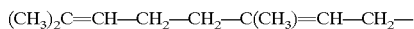

The above compound preferably includes terpenes, their isomers or derivatives of these compounds.

The geranyl group includes both α- and β-isomers, and, as the compound, there may be mentioned those represented by the formulae shown below. To be more specific, the compound includes, but is not limited to, monoterpenes ($C_{10}$) each having one geranyl group as its main structure such as geraniol (trans-3,7-dimethyl-2,6-octadien-1-ol: Compound 1) and its ether derivatives [e.g., trans-1-methoxy-3,7-dimethyl-2,6-octadiene (Compound 2)], its isomer nerol (cis-3,7-dimethyl-2,6-octadiene-1 -ol: Compound 3), and its ether derivatives, acid ester derivatives of these compounds [e.g., 3,7-dimethyl-2,6-octadienyl acetate (Compound 4)], acid derivatives [e.g., 3,7-dimethyl-2,6-octadienoic acid (Compound 5)] and acid ester derivatives, and trans,cis-3, 7-dimethyl-2,6-octadiene (Compounds 6 and 7).

Examples of sesquiterpenes ($C_{15}$) each having one geranyl group include, but are not limited to, α- and β-farnesol (3,7,11-trimethyl-2,6,10-dodecatrien-1-ol: its β-isomer is shown as Compound 8) and its ether derivatives or acid ester derivatives, farnesoate (3,7,11-trimethyl-2,6,10-dodecatrienoic acid: Compound 9) and its acid ester derivatives, farnesyl acetate (3,7,11 -trimethyl-2,6,10-dodecatrienyl acetate: Compound 10), (α-farnesene (3,7,11-trimethyl-1,3,6,10-dodecatetraene), β-farnesene (7,11-dimethyl-3-methylene-1,6,10-dodecatriene: Compound 11), nerolidol (3,7,11-trimethyl-1,6,10-dodecatriene-3-ol: Compound 12).

As examples of the terpenes having two or more geranyl groups, there may be mentioned diterpenes ($C_{20}$), sesterterpenes ($C_{25}$) and triterpenes ($C_{30}$). The diterpenes include, for example, geranylgeraniol (3,7,11,15-tetramethyl-2,6,10, 14-hexadecatetraen-1-ol: Compound 13) and its isomers and derivatives.

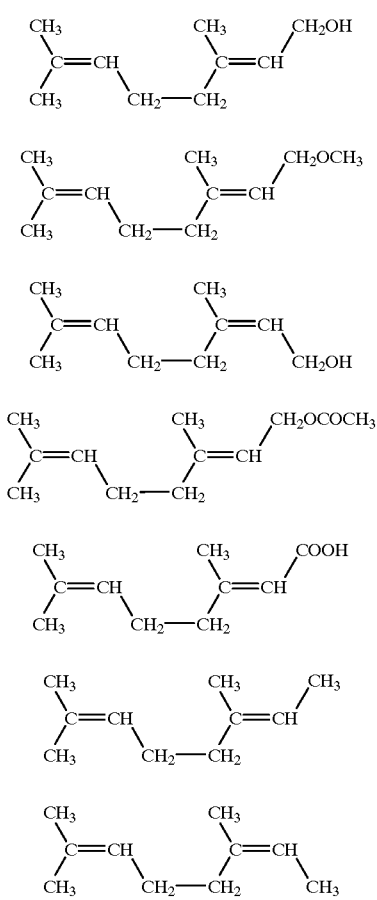

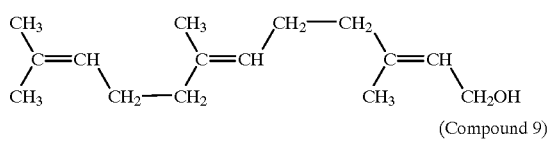

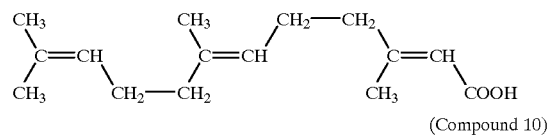

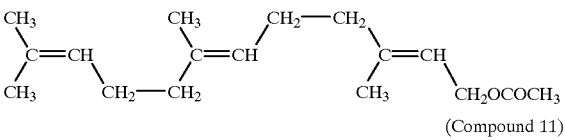

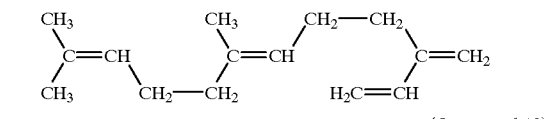

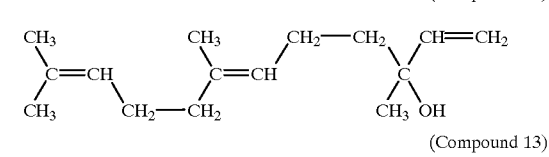

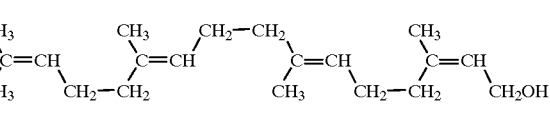

In accomplishing the present invention, the present inventors focused the fact that the aforementioned *Candida albicans*, a typical example of dimorphic fungi transits its form from yeast form to mycelial form, and then from mycelial form once again to yeast form (yeast form→mycelial form→yeast form) and supposed that *Candida albicans* itself secretes a regulatory substance for the morphological transition. Based upon these suppositions, they experimented regarding the possibility of the presence of autoregulatory substances, and detected no substances having inhibitory activity on the morphological transition to mycelial form cells in an extract from homogenized yeast form cells but found that the direct use of a supernatant of a culture solution after the re-transition from mycelial form to yeast form inhibits the transition to mycelial form cells at a rate of equal to or more than about 65%.

The supernatant had a pH of 4.5. As a pH of 4.5 is a transitional condition of *Candida albicans* from mycelial form to yeast form (<pH 7.0), a preparation obtained by adjusting the pH of the supernatant to pH 7.0, which is a transitional condition (=pH 7.0) from yeast form to mycelial form was further studied to find that it has almost equivalent inhibitory effect as above. In addition, effects of nutritional components of a GI (germination-induction) medium (K.-B., Oh., et al., J. Med. Vet. Mycol. 33, 191–195) were examined. None of the nutritional components affected the inhibitory activity on mycelial form cells, verifying that the inhibitory activity on mycelial form cells is affected by neither pH nor nutritional components of a GI medium.

These findings suggested the presence of a substance participating in the morphological transition in a supernatant obtained after re-transition from mycelial form to yeast form, and attempts were made to isolate and identify such a substance. Consequently, the substance was identified as the aforementioned farnesoate, Compound 9 (3,7,11-trimethyl-2,6,10-dodecatrienoic acid). In the isolation and identification were used various devices including reverse phase chromatograph, gas chromatograph, mass spectrograph and NMR analyzers. However, detailed procedures of the isolation and identification are omitted herein.

In addition to farnesoate, the present inventors selected some of the aforementioned compounds, studied their inhibitory activities on the morphological transition and found that any of these compounds had inhibitory activities on the morphological transition, indicating that terpenes or their isomers or derivatives each containing at least one geranyl group as its main structure are effective for inhibition of the morphological transition of dimorphic fungi. The present invention has been accomplished based upon these findings.

When the aforementioned compounds are used as inhibitory agents for the morphological transition of dimorphic fungi, any route of administration can be chosen, including, but not limited to, oral administration, hypodermic injection, intravenous injection and local administration. As examples of the dosage form, there may mentioned powder, tablets, subtle granules, pills, capsules, granules and other oral preparations, instillation, injections, suppositories and other parenteral (non-oral) preparations. These preparations can be prepared by using any of pharmaceutically acceptable carriers, excipients and other additives. The pharmaceutically acceptable carriers, excipients include, for instance, glucose, lactose, gelatin, mannitol, starch paste, magnesium trisilicate, corn starch, keratin and colloidal silica. In addition, any of stabilizers, expanders, colorants, flavors and other auxiliaries can be added to the preparations. These preparations can be produced in accordance with any conventional methods known to one skilled in the art.

The target dimorphic fungi to which the agent of the invention is effective include, in addition to the genus Candida including the aforementioned Candida albicans, C. stellatoidea, C. tropicalis, C. grabrata and C. parapsilosis, genus Cryptococcus such as Cryptococcus neoformans, genus Sporothrix such as Sporothrix schenckii, and genus Histoplasma such as Histoplasma capsulatum.

The present invention will be further illustrated in detail with reference to several inventive examples (experimental examples) below which are not directed to limiting the scope of the invention.

EXPERIMENTAL EXAMPLE 1
<Verification Test on Inhibitory Activity of Farnesoate on Y to M Transition>

Candida albicans strain ATCC 10231 is used as a microbe to be tested. Initially, a slant medium is prepared with 5 ml of potato dextrose agar (PDA) in a 20-ml test tube, onto which the test microbe in yeast form is then inoculated using a platinum spatula to give a preservation slant. The microbe on the preservation slant is incubated over one week or more, and sufficiently grown yeast form cells are then harvested and subjected to the test.

The obtained test microbe is inoculated on a 200 ml YPD (1% yeast extract, 2% Bacto (registered trade mark) peptone, 2% glucose) medium using a platinum spatula, and then subjected to preincubation at 25° C. for 48 hours with shaking (120 rpm). Next, yeast cells are harvested by centrifugation (4° C., 3000 rpm) and washed three times with sterile distilled water. The cells are then re-suspended into sterile distilled water and allowed to stand at 4° C. for 3 days to give starved yeast form cells.

These starved yeast form cells are counted using a hemocytometer (Thoma's hemocytometer: manufactured by Kayagaki Irika Kogyo K.K., Japan), and inoculated in a concentration of $1.0 \times 10^6$ cells/ml to 2 ml of a GS medium (composition per 1000 ml (by weight): glucose 5, $Na_2HPO_4 \cdot 12H_2O$ 0.26, $KH_2PO_4$ 0.66, $NH_4Cl$ 0.33, $MgSO_4 \cdot 7H_2O$ 0.88, biotin 16 $\mu$) in a plastic dish (3.5 cm diameter). The medium has been adjusted in advance to a pH of 7.0 with 5N—NaOH.

For the transition to mycelial form cells, the yeast form cells are subjected to stationary culture at 37° C. to induce mycelial form.

As farnesoate (Compound 9), the aforementioned purified and identified compound is used in this test, whereas a commercially available farnesoate has been verified to have equivalent effects in another test. The farnesoate is dissolved in dimethyl sulfoxide (DMSO) to a final concentration of 25 $\mu$g/ml, and added to the medium. The concentration of DMSO in the medium is adjusted to 0.5% V/V.

The time immediately after transferring the dish to the culture at 37° C. is defined as zero time and the cells are then subjected to chronological morphological observation with an inverted microscope (OLYMPUS, Japan) at intervals of 1 to 2 hours. In the observation, cell number is counted at random, and the proportion of mycelial form cells in the counted cells is defined as the rate of Y to M transition (%) as an index of activity assessment.

The mycelial form cells are defined as the cells each having a distance from the tip of its germ tube to the end of the cell of 2a where a yeast form cell is assumed to be an ellipse and the length of its minor axis is defined as "a", or apical mycelia of cells whose true mycelia continuously grow and no mother yeast form cells are found. The yeast form cells after re-transition from mycelial form cells also include cells whose true mycelia have constriction on their tips. As comparative references, a sample where no components are added to the medium in a culture dish (Control) and a sample where DMSO alone is added to the medium (DMSO) are prepared. FIG. 1A demonstrates the results of the above test, and FIGS. 1B and 1C represent microphotographs respectively illustrating Control and the sample added with farnesoate, both after 8 hours of incubation.

The results demonstrate that farnesoate allows the transition of yeast form cells to mycelial form cells but also promotes the re-transition of the transited mycelial form cells to yeast form cells.

EXPERIMENTAL EXAMPLE 2
<Assessment Tests of Inhibitory Activities of Farnesoate on Y to M Transition and Inhibitory Effect on Yeast Form Cells>

A series of starved yeast form cells are prepared on media in dishes in a similar manner as in Experimental Example 1, and to each of these cultures is added a farnesoate solution in DMSO each having a concentration of 0, 0.1, 0.2, 0.4, 0.8, 1.6, 3.2, 6.25, 12.5, 25, 50, 100 or 200 $\mu$g/ml. In a similar manner as in Experimental Example 1, the inhibitory effect on yeast form cells (growth rate of yeast form cell) and inhibitory effect on Y to M transition (transition rate of yeast form cells to mycelial form cells) are determined after transferring the cultures to 37° C.

FIG. 2 demonstrates the inhibitory effect on yeast form cells after 8 hours of incubation at 37° C., indicating that farnesoate has a 50% inhibitory concentration ($IC_{50}$) of 200 $\mu$g/ml or higher on yeast form cells.

Figure 3:
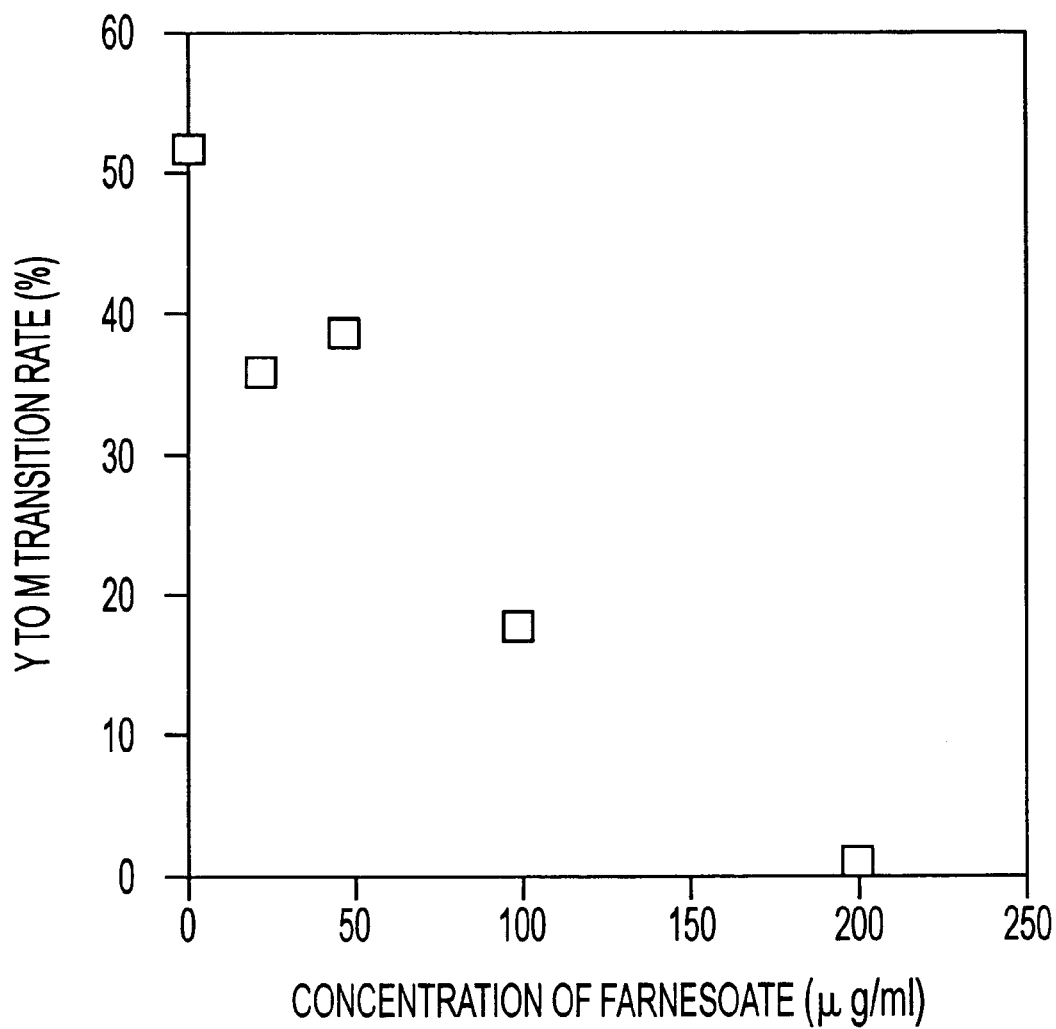
FIG. 3 is a diagram graphically illustrating inhibitory effect of famesoate on the transition of yeast form cells to mycelial form cells (hereinafter briefly referred to as "Y to M transition") after 2 hours of incubation.

FIG. 3 demonstrates the inhibitory effect on Y to M form transition (inhibitory rate of Y to M transition) after 2 hours of incubation at 37° C., indicating that farnesoate in a concentration of 100 μg/ml can exhibit inhibitory effect on Y to M transition (promoting activity on M to Y transition) more than 50% after 2 hours of incubation; and that the 50% inhibitory concentration of farnesoate is as small as 3.2 μg/ml on Y to M transition (promoting activity on M to Y transition after 5 hours of incubation.

EXPERIMENTAL EXAMPLE 3
<Assessment Tests of Farnesol, Farnesyl Acetate and β-Farnesene>

Figure 4:
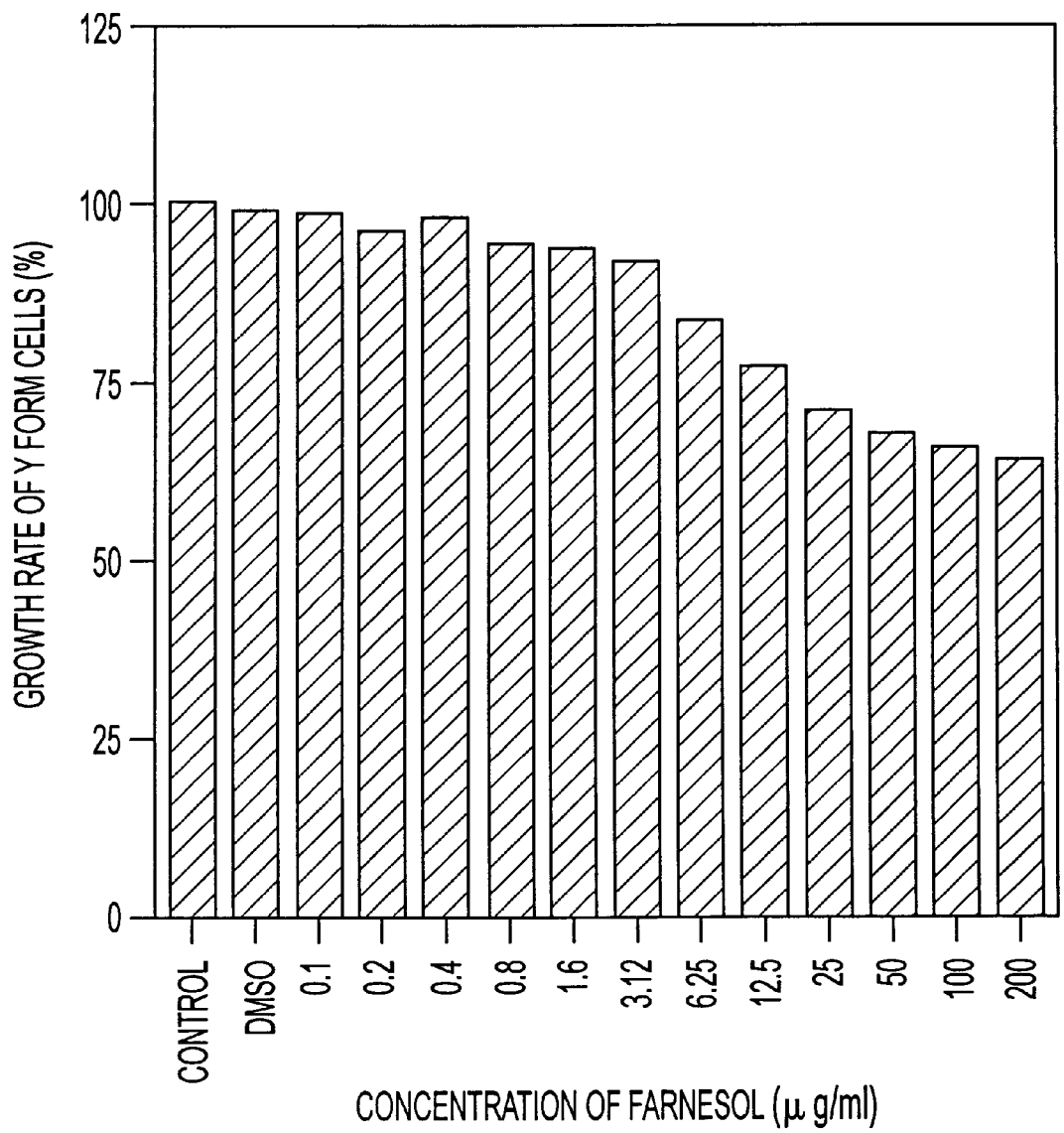
FIG. 4 is a diagram graphically illustrating inhibitory effect of farnesol on the growth of yeast form cells after 8 hours of incubation.
Figure 5:
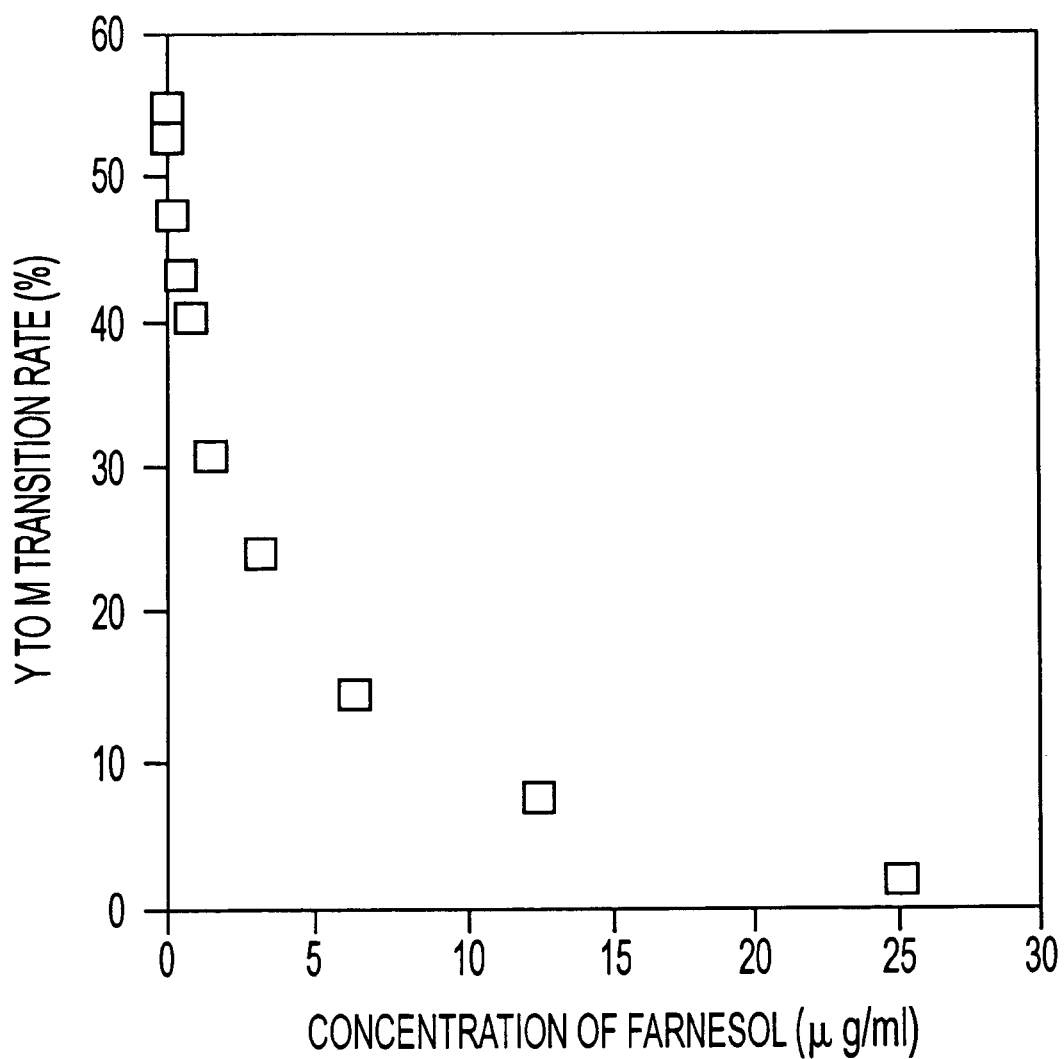
FIG. 5 is a diagram graphically illustrating inhibitory effect of farnesol on Y to M transition after 2 hours of incubation.
Figure 6:
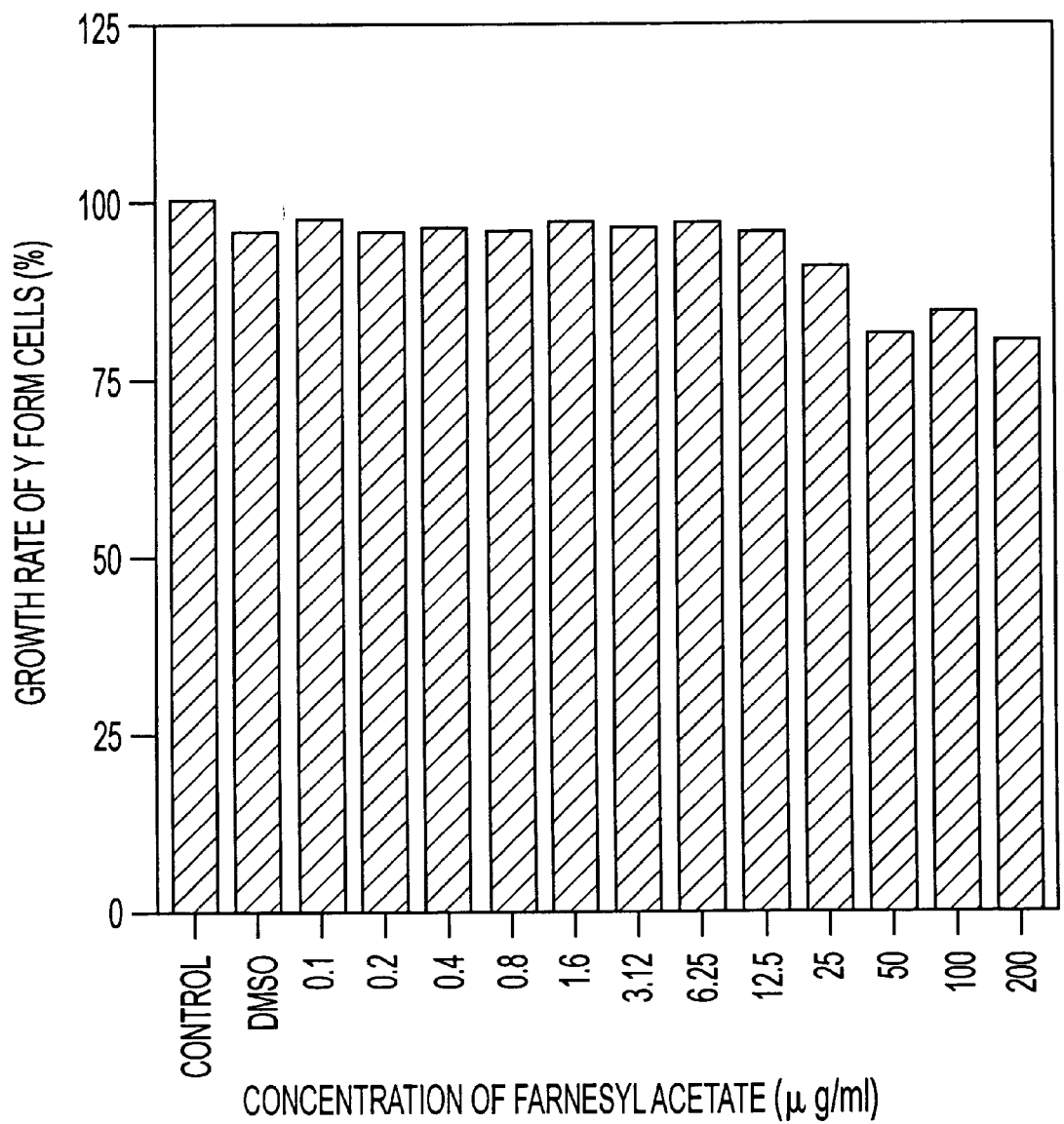
FIG. 6 is a diagram graphically illustrating inhibitory effect of farnesyl acetate on the growth of yeast form cells after 8 hours of incubation.
Figure 7:
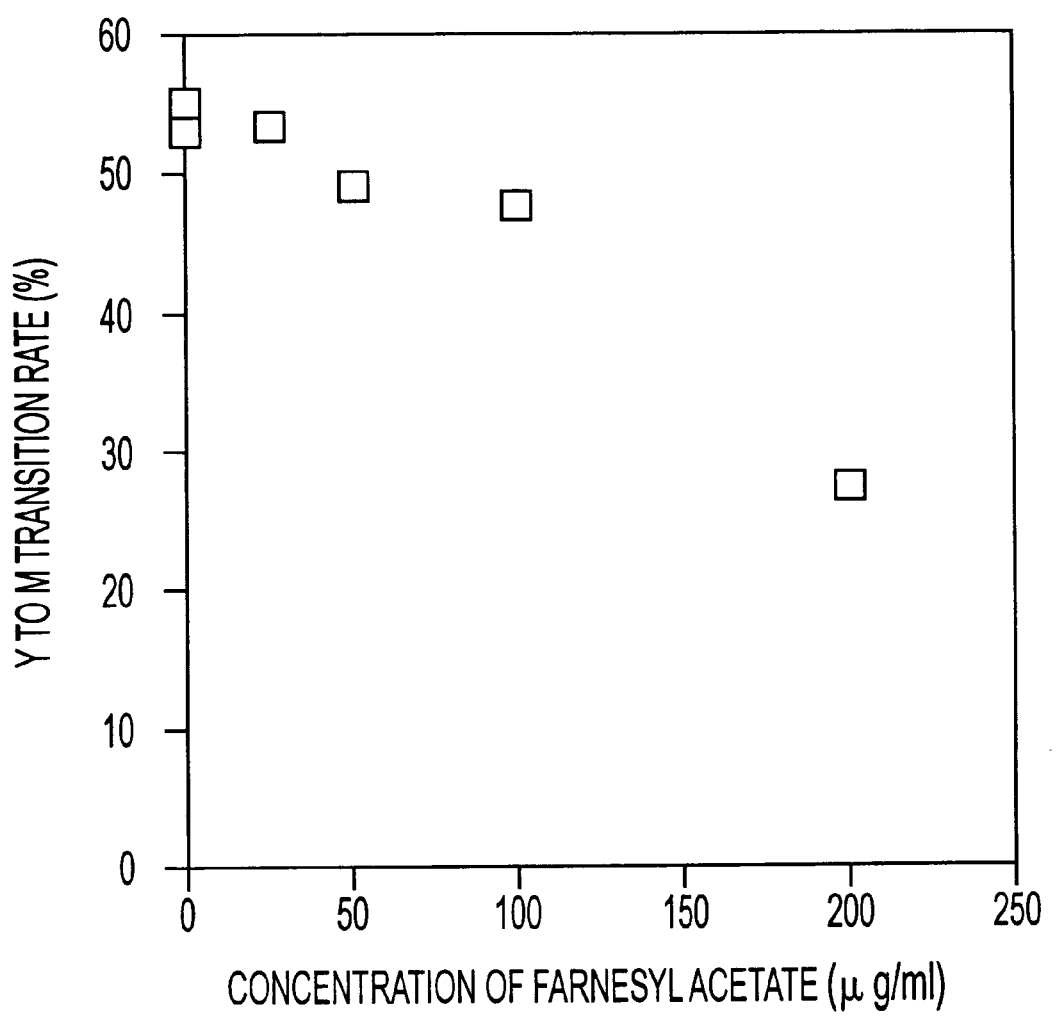
FIG. 7 is a diagram graphically illustrating inhibitory effect of farnesyl acetate on Y to M transition after 2 hours of incubation.
Figure 8:
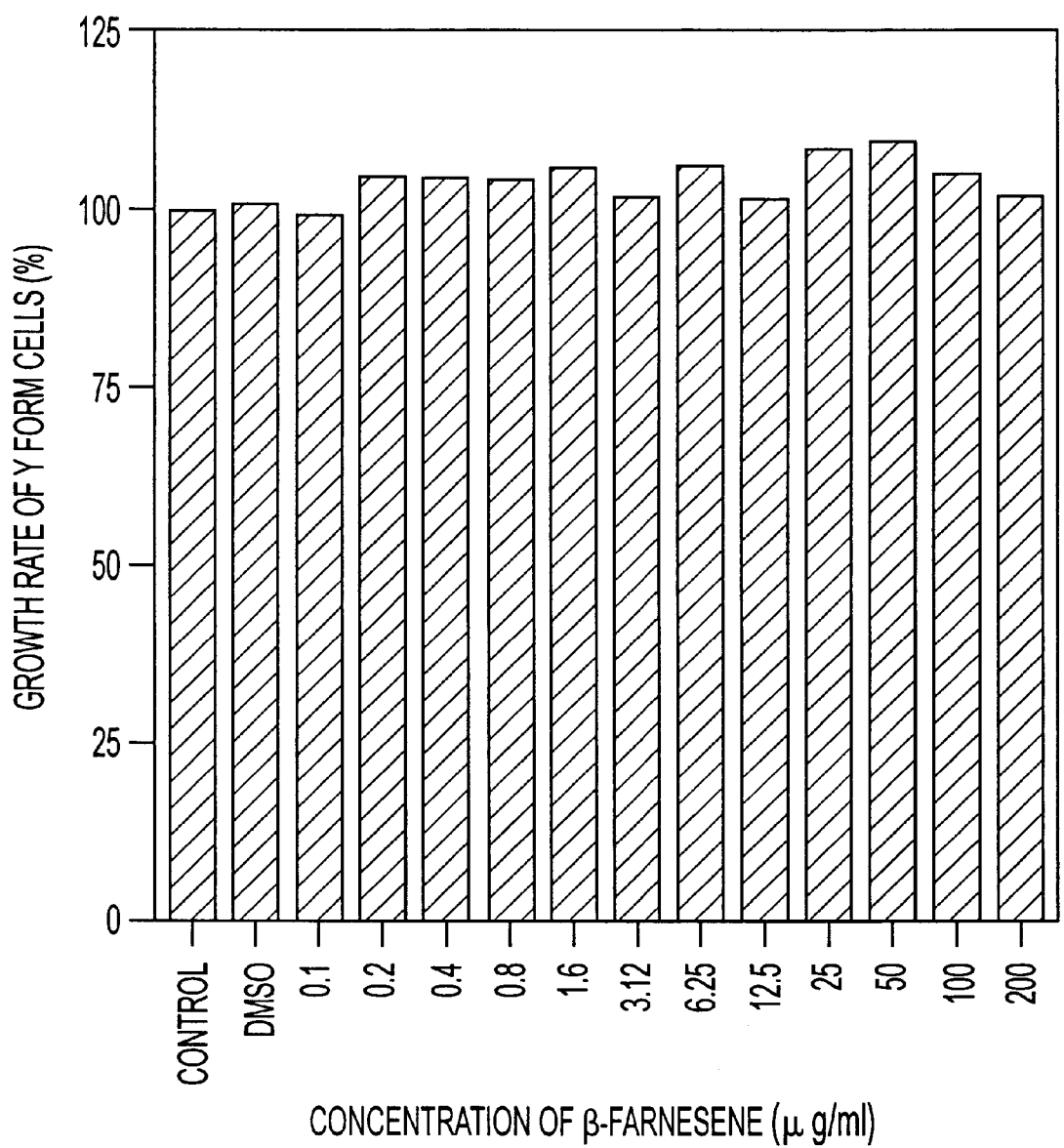
FIG. 8 is a diagram graphically illustrating inhibitory effect of β-farnesene on the growth of yeast form cells after 8 hours of incubation.
Figure 9:
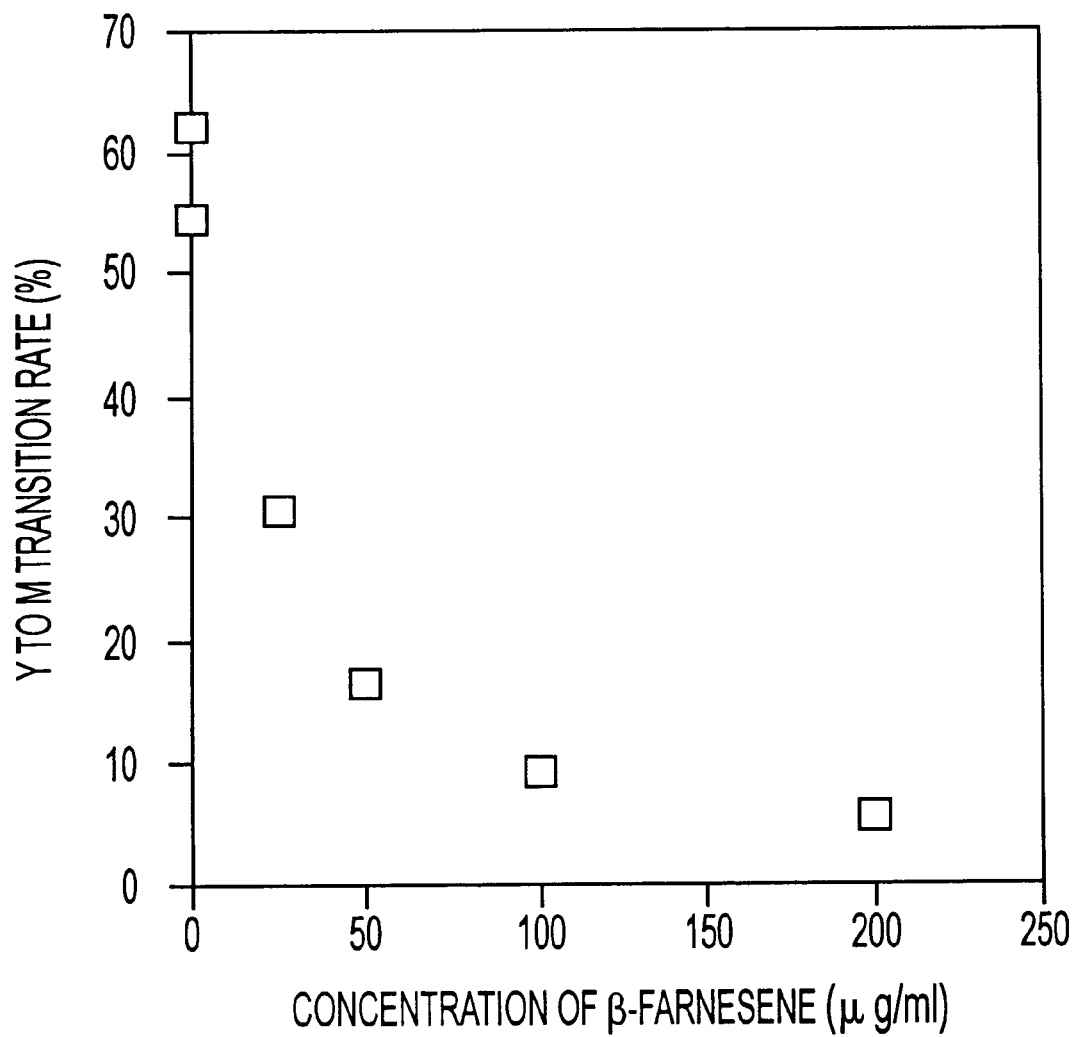
FIG. 9 is a diagram graphically illustrating inhibitory effect of β-farnesene on Y to M transition after 2 hours of incubation.

Under the same conditions as in Experimental Example 2, farnesol (Compound 8), farnesyl acetate (Compound 10) and β-farnesene (Compound 11) are respectively subjected to tests and their activities are assessed. Commercially available reagents are used as the above compounds in the tests. FIGS. 4, 6 and 8 respectively demonstrate the inhibitory effects of individual compounds on yeast form cells after 8 hours of incubation, and FIGS. 5, 7 and 9 individually illustrate the inhibitory effect on Y to M transition of each compound after 2 hours of incubation. FIG. 10 demonstrates 50% inhibitory concentrations of the individual compounds on yeast form cells after 8 hours of incubation, and their 50% inhibitory concentrations on Y to M transition after 2 hours of and after 5 hours of incubation. These results demonstrate that any of the compounds tested has a high 50% inhibitory concentration of 200 μg/ml or more on yeast form cells, but a low 50% inhibitory concentration on Y to M transition, indicating that these compounds have low fungicide effect but high inhibitory activity on Y to M transition (promoting activity on M to Y transition).

EXPERIMENTAL EXAMPLE 4
<Assessment Tests on Geraniol and Geranylgeraniol>

Geraniol (Compound 1) and geranylgeraniol (Compound 13) are respectively subjected to tests in a similar manner as in Experimental Example 2, and their activities are assessed. Commercially available reagents are used as the above compounds in the tests. As illustrated in FIG. 10, these compounds have low inhibitory effect on yeast form cells yet high inhibitory activity on Y to M transition.

All the results mentioned above demonstrate that terpenes each having at least one geranyl group as its main structure exhibit regulatory activity on mycelial form cells (promoting activity on M to Y transition) of dimorphic fungi.

Other embodiments and variations will be obvious to those skilled in the art.

What is claimed is:

1. A method for regulating the morphological transition of dimorphic Candida in a patient, comprising administering orally or by injection a compound to a patient suffering from an infecton caused by dimorphic Candida selected from the group consisting of *Candida albicans, Candida stellatoidea, Candida tropicalis, Candida grabrata*, and *Candida parapsilosis*, to regulatee the morphological transition of said dimorphic Candida, wherein the compound is selected from the group consisting of:

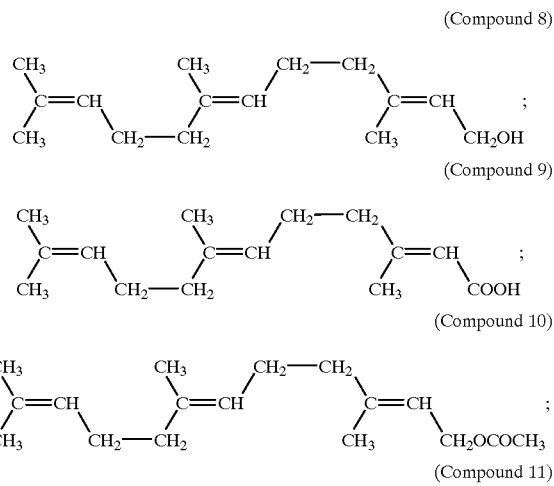

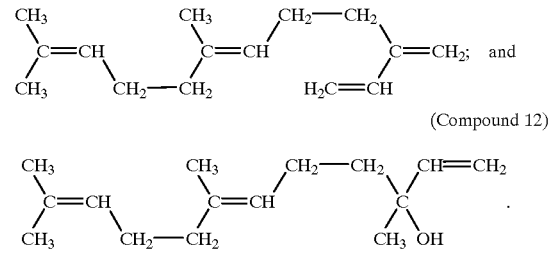

* * * * *